(12) United States Patent
Arbefeuille

(10) Patent No.: US 12,048,622 B2
(45) Date of Patent: Jul. 30, 2024

(54) VASCULAR PROSTHESIS WITH MOVEABLE FENESTRATION AND METHOD OF USE

(71) Applicant: Bolton Medical, Inc., Sunrise, FL (US)

(72) Inventor: Samuel Arbefeuille, Sunrise, FL (US)

(73) Assignee: Bolton Medical, Inc., Sunrise, FL (US)

( * ) Notice: Subject to any disclaimer, the term of this patent is extended or adjusted under 35 U.S.C. 154(b) by 234 days.

(21) Appl. No.: 17/838,806

(22) Filed: Jun. 13, 2022

(65) Prior Publication Data

US 2022/0304798 A1    Sep. 29, 2022

Related U.S. Application Data

(60) Division of application No. 16/391,843, filed on Apr. 23, 2019, now Pat. No. 11,369,466, which is a
(Continued)

(51) Int. Cl.
| | | |
|---|---|---|
| *A61F 2/07* | (2013.01) | |
| *A61F 2/89* | (2013.01) | |
| *A61F 2/06* | (2013.01) | |

(52) U.S. Cl.
CPC ............... *A61F 2/07* (2013.01); *A61F 2/89* (2013.01); *A61F 2002/061* (2013.01);
(Continued)

(58) Field of Classification Search
CPC .......... A61F 2002/061; A61F 2002/067; A61F 2002/065; A61F 2002/826;
(Continued)

(56) References Cited

U.S. PATENT DOCUMENTS

| | | |
|---|---|---|
| 4,787,391 A | 11/1988 | Elefteriades |
| 5,123,917 A | 6/1992 | Lee |

(Continued)

FOREIGN PATENT DOCUMENTS

| | | |
|---|---|---|
| CN | 104066401 A | 9/2014 |
| CN | 203815663 U | 9/2014 |

(Continued)

OTHER PUBLICATIONS

International Search Report and Written Opinion for Application No. PCT/US2022/033239 Nov. 7, 2022.
(Continued)

*Primary Examiner* — Katherine H Schwiker
(74) *Attorney, Agent, or Firm* — Stephen J. Kenny; Foley Hoag LLP

(57) ABSTRACT

Vascular prosthesis includes a luminal graft component defining a graft fenestration, at least one support disk fenestration, and a moveable disk defining a moveable disk opening, wherein the graft fenestration, the support disk fenestration and the moveable disk opening are all aligned, and the moveable disk is sandwiched between the support disk and the luminal graft component or between two of the support disks. The moveable disk is moveable between the support disk and the luminal graft component. The support disk is fixed to the luminal graft component. The vascular prosthesis is implanted by a method that includes directing the vascular prosthesis to an aneurysm site of a patient, and then implanting a branch prosthesis through the graft fenestration and into an arterial branch, whereby the moveable disk opening moves within the support disk fenestration to properly align the branch prosthesis with the arterial branch.

16 Claims, 8 Drawing Sheets

Related U.S. Application Data continuation of application No. PCT/US2018/019353, filed on Feb. 23, 2018.

(60) Provisional application No. 62/463,049, filed on Feb. 24, 2017.

(52) U.S. Cl.
CPC ... *A61F 2002/072* (2013.01); *A61F 2002/075* (2013.01); *A61F 2220/005* (2013.01); *A61F 2220/0075* (2013.01); *A61F 2230/0054* (2013.01); *A61F 2250/006* (2013.01)

(58) Field of Classification Search
CPC .......... A61F 2002/828; A61F 2002/852; A61F 2002/856; A61F 2250/006; A61F 2002/072; A61F 2002/075; A61F 2002/077; A61F 2/07; A61F 2/89; A61F 2220/0075; A61F 2230/0054
See application file for complete search history.

(56) References Cited

U.S. PATENT DOCUMENTS

| | | |
|---|---|---|
| 5,242,452 A | 9/1993 | Inoue |
| 5,507,769 A | 4/1996 | Marin et al. |
| 5,713,948 A | 2/1998 | Uflacker |
| 5,755,769 A | 5/1998 | Richard et al. |
| 5,873,906 A | 2/1999 | Lau et al. |
| 6,113,623 A | 9/2000 | Sgro |
| 6,171,334 B1 | 1/2001 | Cox |
| 6,280,464 B1 | 8/2001 | Hayashi |
| 6,352,561 B1 | 3/2002 | Leopold et al. |
| 6,395,018 B1 | 5/2002 | Castaneda |
| 6,610,087 B1 | 8/2003 | Zarbatany et al. |
| 6,645,242 B1 | 11/2003 | Quinn |
| 6,776,791 B1 | 8/2004 | Stallings et al. |
| 7,112,216 B2 | 9/2006 | Gregorich |
| 7,189,257 B2 | 3/2007 | Schmitt et al. |
| 7,435,253 B1 | 10/2008 | Hartley et al. |
| 7,637,940 B2 | 12/2009 | Kocur et al. |
| 7,645,298 B2 | 1/2010 | Hartley et al. |
| 7,763,063 B2 | 7/2010 | Arbefeuille et al. |
| 7,842,081 B2 | 11/2010 | Yadin |
| 8,007,605 B2 | 8/2011 | Arbefeuille et al. |
| 8,062,345 B2 | 11/2011 | Ouellette et al. |
| 8,062,346 B2 | 11/2011 | Quigley et al. |
| 8,062,349 B2 | 11/2011 | Moore et al. |
| 8,070,790 B2 | 12/2011 | Berra et al. |
| 8,128,686 B2 | 3/2012 | Paul, Jr. et al. |
| 8,172,895 B2 | 5/2012 | Anderson et al. |
| 8,236,040 B2 | 8/2012 | Mayberry et al. |
| 8,277,501 B2 | 10/2012 | Chalekian et al. |
| 8,292,943 B2 | 10/2012 | Berra et al. |
| 8,298,278 B2 | 10/2012 | Gregorich et al. |
| 8,308,790 B2 | 11/2012 | Arbefeuille et al. |
| 8,333,800 B2 | 12/2012 | Bruszewski et al. |
| 8,343,211 B2 | 1/2013 | Gregorich et al. |
| 8,377,113 B2 | 2/2013 | Hartley et al. |
| 8,449,595 B2 | 5/2013 | Ouellette et al. |
| 8,470,018 B2 | 6/2013 | Hartley et al. |
| 8,480,725 B2 | 7/2013 | Rasmussen et al. |
| 8,480,728 B2 | 7/2013 | Gregorich et al. |
| 8,486,129 B2 | 7/2013 | Lautherjung |
| 8,500,792 B2 | 8/2013 | Berra |
| 8,506,622 B2 | 8/2013 | Bruszewski et al. |
| 8,636,788 B2 | 1/2014 | Arbefeuille et al. |
| 8,641,752 B1 | 2/2014 | Holm et al. |
| 8,740,963 B2 | 6/2014 | Arbefeuille et al. |
| 8,808,351 B2 | 8/2014 | Osborne |
| 8,915,955 B2 | 12/2014 | West et al. |
| 8,926,693 B2 | 1/2015 | Duffy et al. |
| 9,101,455 B2 | 8/2015 | Roeder et al. |
| 9,101,506 B2 | 8/2015 | Arbefeuille et al. |
| 9,173,755 B2 | 11/2015 | Berra et al. |
| 9,198,786 B2 | 12/2015 | Moore et al. |
| 9,220,617 B2 | 12/2015 | Berra |
| 9,259,336 B2 | 2/2016 | Schaeffer et al. |
| 9,320,631 B2 | 4/2016 | Moore et al. |
| 9,333,104 B2 | 5/2016 | Ouellette et al. |
| 9,358,142 B2 | 6/2016 | Johnson |
| 9,364,314 B2 | 6/2016 | Berra et al. |
| 9,408,734 B2 | 8/2016 | Arbefeuille et al. |
| 9,408,735 B2 | 8/2016 | Arbefeuille et al. |
| 9,439,751 B2 | 9/2016 | White et al. |
| 9,561,124 B2 | 2/2017 | Arbefeuille et al. |
| 9,592,112 B2 | 3/2017 | Arbefeuille et al. |
| 9,655,712 B2 | 5/2017 | Berra et al. |
| 9,770,322 B2 | 9/2017 | Burkart et al. |
| 9,827,123 B2 | 11/2017 | Arbefeuille et al. |
| 9,839,542 B2 | 12/2017 | Bruszewski et al. |
| 9,861,503 B2 | 1/2018 | Barthold et al. |
| 9,877,857 B2 | 1/2018 | Arbefeuille et al. |
| 9,907,686 B2 | 3/2018 | Ouellette et al. |
| 9,913,743 B2 | 3/2018 | Arbefeuille et al. |
| 9,925,080 B2 | 3/2018 | Arbefeuille et al. |
| 10,004,620 B2 | 6/2018 | Treacy et al. |
| 10,005,269 B2 | 6/2018 | Hall et al. |
| 10,080,674 B2 | 9/2018 | Yuan et al. |
| 10,105,248 B2 | 10/2018 | Berra et al. |
| 10,105,250 B2 | 10/2018 | Berra |
| 10,182,930 B2 | 1/2019 | Moore et al. |
| 10,213,291 B2 | 2/2019 | Berra et al. |
| 10,245,137 B2 | 4/2019 | Scutti et al. |
| 10,265,202 B2 | 4/2019 | Greenberg et al. |
| 10,299,951 B2 | 5/2019 | Arbefeuille et al. |
| 10,307,275 B2 | 6/2019 | Berra et al. |
| 10,390,930 B2 | 8/2019 | Arbefeuille et al. |
| 10,478,320 B2 | 11/2019 | Shahriari |
| 10,485,684 B2 | 11/2019 | Marmur et al. |
| 10,512,556 B2 | 12/2019 | Longo et al. |
| 10,617,542 B2 | 4/2020 | Chakfe et al. |
| 10,702,406 B2 | 7/2020 | Swift et al. |
| 10,744,012 B2 | 8/2020 | Bonsignore et al. |
| 10,898,357 B2 | 1/2021 | Arbefeuille et al. |
| 10,987,235 B2 | 4/2021 | Eubanks et al. |
| 10,987,873 B2 | 4/2021 | Moldave et al. |
| 11,000,359 B2 | 5/2021 | Torrance et al. |
| 11,219,540 B2 | 1/2022 | Arbefeuille |
| 11,278,390 B2 | 3/2022 | Lostetter |
| 11,291,572 B2 | 4/2022 | Garcia |
| 11,351,025 B2 | 6/2022 | Lostetter |
| 11,369,466 B2 | 6/2022 | Arbefeuille |
| 11,399,929 B2 | 8/2022 | Arbefeuille |
| 11,413,177 B2 | 8/2022 | Lostetter |
| 11,547,584 B2 | 1/2023 | Lostetter |
| 11,779,454 B2 | 10/2023 | Arbefeuille |
| 11,801,129 B2 | 10/2023 | Lostetter |
| 2002/0038144 A1 | 3/2002 | Trout et al. |
| 2002/0062133 A1 | 5/2002 | Gilson et al. |
| 2002/0151956 A1 | 10/2002 | Chobotov et al. |
| 2002/0177890 A1 | 11/2002 | Lenker |
| 2002/0188344 A1 | 12/2002 | Bolea et al. |
| 2002/0193872 A1 | 12/2002 | Trout et al. |
| 2004/0059406 A1 | 3/2004 | Cully et al. |
| 2004/0073289 A1 | 4/2004 | Hartley |
| 2004/0138737 A1 | 7/2004 | Davidson et al. |
| 2005/0102021 A1 | 5/2005 | Osborne |
| 2005/0102023 A1 | 5/2005 | Yadin et al. |
| 2005/0119722 A1 | 6/2005 | Styrc et al. |
| 2005/0131517 A1 | 6/2005 | Hartley et al. |
| 2005/0131518 A1 | 6/2005 | Hartley et al. |
| 2005/0131519 A1 | 6/2005 | Hartley |
| 2005/0131523 A1 | 6/2005 | Bashiri et al. |
| 2005/0154444 A1 | 7/2005 | Quadri |
| 2005/0171597 A1 | 8/2005 | Boatman et al. |
| 2006/0015171 A1 | 1/2006 | Armstrong |
| 2006/0020319 A1 | 1/2006 | Kim et al. |
| 2006/0095118 A1 | 5/2006 | Hartley |
| 2006/0155359 A1 | 7/2006 | Watson |
| 2006/0184226 A1 | 8/2006 | Austin |
| 2006/0247760 A1 | 11/2006 | Ganesan et al. |
| 2006/0247761 A1 | 11/2006 | Greenberg et al. |
| 2007/0021822 A1 | 1/2007 | Boatman |

(56) References Cited

U.S. PATENT DOCUMENTS

| | | |
|---|---|---|
| 2007/0055358 A1 | 3/2007 | Krolik et al. |
| 2007/0055360 A1 | 3/2007 | Hanson et al. |
| 2007/0112418 A1 | 5/2007 | Eidenschink et al. |
| 2007/0135904 A1 | 6/2007 | Eidenschink et al. |
| 2007/0208414 A1 | 9/2007 | Sorenson et al. |
| 2007/0208419 A1 | 9/2007 | Meyer et al. |
| 2007/0213805 A1 | 9/2007 | Schaeffer et al. |
| 2007/0233223 A1 | 10/2007 | Styrc |
| 2007/0244542 A1 | 10/2007 | Greenan et al. |
| 2007/0244547 A1 | 10/2007 | Greenan |
| 2008/0091260 A1 | 4/2008 | Pomeranz et al. |
| 2008/0132988 A1 | 6/2008 | Jordan |
| 2008/0264102 A1 | 10/2008 | Berra |
| 2009/0030502 A1 | 1/2009 | Sun et al. |
| 2009/0043377 A1 | 2/2009 | Greenberg et al. |
| 2009/0048663 A1 | 2/2009 | Greenberg |
| 2009/0248135 A1 | 10/2009 | Bruszewski et al. |
| 2009/0264990 A1 | 10/2009 | Bruszewski et al. |
| 2010/0004730 A1 | 1/2010 | Benjamin et al. |
| 2010/0057186 A1 | 3/2010 | West et al. |
| 2010/0063576 A1 | 3/2010 | Schaeffer et al. |
| 2010/0121429 A1 | 5/2010 | Greenan et al. |
| 2010/0268319 A1 | 10/2010 | Bruszewski et al. |
| 2010/0316830 A1 | 12/2010 | Hartley et al. |
| 2011/0077730 A1 | 3/2011 | Fenster |
| 2011/0190862 A1 | 8/2011 | Bashiri et al. |
| 2011/0257720 A1 | 10/2011 | Peterson et al. |
| 2012/0022630 A1 | 1/2012 | Wubbeling |
| 2012/0035714 A1 | 2/2012 | Ducke et al. |
| 2012/0172965 A1 | 7/2012 | Kratzberg et al. |
| 2012/0191174 A1 | 7/2012 | Vinluan et al. |
| 2012/0296360 A1 | 11/2012 | Norris et al. |
| 2013/0116773 A1 | 5/2013 | Roeder et al. |
| 2013/0116775 A1 | 5/2013 | Roeder et al. |
| 2013/0123900 A1 | 5/2013 | Eblacas et al. |
| 2013/0158648 A1 | 6/2013 | Hartley et al. |
| 2013/0211505 A1 | 8/2013 | Robison |
| 2013/0282102 A1 | 10/2013 | Peterson |
| 2013/0289696 A1 | 10/2013 | Maggard et al. |
| 2013/0289713 A1 | 10/2013 | Pearson et al. |
| 2014/0046428 A1 | 2/2014 | Cragg et al. |
| 2014/0180378 A1 | 6/2014 | Roeder |
| 2014/0324150 A1 | 10/2014 | Stephens et al. |
| 2015/0105819 A1 | 4/2015 | Becking et al. |
| 2015/0105849 A1 | 4/2015 | Cohen et al. |
| 2015/0105850 A1 | 4/2015 | Shahriari |
| 2015/0202065 A1 | 7/2015 | Shalev et al. |
| 2015/0202067 A1 | 7/2015 | Barrand et al. |
| 2015/0216686 A1 | 8/2015 | Chakfe et al. |
| 2015/0335452 A1 | 11/2015 | Rao et al. |
| 2016/0100969 A1 | 4/2016 | Lesmeister et al. |
| 2016/0106564 A1 | 4/2016 | Roeder et al. |
| 2016/0120667 A1 | 5/2016 | Bolduc et al. |
| 2016/0184078 A1 | 6/2016 | Choubey et al. |
| 2016/0199207 A1 | 7/2016 | Treacy et al. |
| 2016/0296353 A1 | 10/2016 | Skender |
| 2016/0302950 A1 | 10/2016 | Marmur et al. |
| 2017/0281382 A1 | 10/2017 | Lostetter et al. |
| 2018/0153680 A1 | 6/2018 | Greenberg et al. |
| 2019/0231514 A1 | 8/2019 | Arbefeuille |
| 2019/0231571 A1 | 8/2019 | Lostetter |
| 2019/0247213 A1 | 8/2019 | Lostetter |
| 2019/0269498 A1 | 9/2019 | Arbefeuille et al. |
| 2019/0350694 A1 | 11/2019 | Arbefeuille et al. |
| 2020/0246165 A1 | 8/2020 | Arbefeuille et al. |
| 2020/0352700 A1 | 11/2020 | Torrance et al. |
| 2021/0100669 A1 | 4/2021 | Arbefeuille et al. |
| 2021/0236262 A1 | 8/2021 | Torrance et al. |
| 2022/0087841 A1 | 3/2022 | Arbefeuille |
| 2022/0168091 A1 | 6/2022 | Lostetter |
| 2022/0257361 A1 | 8/2022 | Lostetter |
| 2022/0304798 A1 | 9/2022 | Arbefeuille |
| 2022/0313419 A1 | 10/2022 | Arbefeuille |
| 2022/0378594 A1 | 12/2022 | Lostetter |
| 2022/0395365 A1 | 12/2022 | Lostetter et al. |
| 2023/0063108 A1 | 3/2023 | Magen et al. |
| 2024/0058114 A1 | 2/2024 | Arbefeuille |

FOREIGN PATENT DOCUMENTS

| | | |
|---|---|---|
| CN | 105832447 A | 8/2016 |
| CN | 105943213 A | 9/2016 |
| EP | 1673040 A1 | 6/2006 |
| EP | 2501334 A1 | 9/2012 |
| EP | 2517672 A1 | 10/2012 |
| EP | 2735283 A1 | 5/2014 |
| EP | 2740440 A2 | 6/2014 |
| EP | 2745812 A1 | 6/2014 |
| EP | 2749250 A1 | 7/2014 |
| EP | 2606851 B1 | 11/2015 |
| EP | 3040054 A1 | 7/2016 |
| EP | 3146993 A1 | 3/2017 |
| EP | 3272319 A1 | 1/2018 |
| FR | 2932979 A1 | 1/2010 |
| JP | 2012/152549 A | 8/2012 |
| WO | WO-97/25002 A1 | 7/1997 |
| WO | WO-99/29262 A1 | 6/1999 |
| WO | WO-99/34749 A1 | 7/1999 |
| WO | WO-03/099108 A2 | 12/2003 |
| WO | WO-2006/037086 A1 | 4/2006 |
| WO | WO-2009/148594 A1 | 12/2009 |
| WO | WO-2010/024880 A1 | 3/2010 |
| WO | WO-2010/030370 A1 | 3/2010 |
| WO | WO-2010/127040 A1 | 11/2010 |
| WO | WO-2012/047308 A1 | 4/2012 |
| WO | WO-2012/116368 A2 | 8/2012 |
| WO | WO-2012/145823 A1 | 11/2012 |
| WO | WO-2014/162306 A2 | 10/2014 |
| WO | WO-2015/059019 A1 | 4/2015 |
| WO | WO-2015/070792 A1 | 5/2015 |
| WO | WO-2016/122862 A1 | 8/2016 |
| WO | WO-2017/072168 A1 | 5/2017 |
| WO | WO-2017/218474 A1 | 12/2017 |
| WO | WO-2018/026768 A1 | 2/2018 |
| WO | WO-2018/156849 A1 | 8/2018 |
| WO | WO-2018/156850 A1 | 8/2018 |
| WO | WO-2022/265985 A1 | 12/2022 |
| WO | WO-2022/265989 A1 | 12/2022 |
| WO | WO-2022/265989 A8 | 12/2022 |

OTHER PUBLICATIONS

International Search Report and Written Opinion for International Application No. PCT/US22/33247 dated Sep. 13, 2022.

International Preliminary Report on Patentability for International Application No. PCT/US2018/019353 dated Aug. 27, 2019.

International Search Report and Written Opinion for International Application No. PCT/US2018/019353 dated May 7, 2018.

Luo et al, "Stent-grafts for the treatment of TIPS dysfunction: Fluency stent vs. Wallgrent stent," World J Gastroenterol, 19(30): 5000-5005 (2013).

Wang et al. "Preliminary experimental study on a novel adjustable sutureless aortic prosthesis" Chinese Journal of Experimental Surgery, 23(11): 1325-1327 w/ English Abstract (2006).

VASCULAR PROSTHESIS WITH MOVEABLE FENESTRATION AND METHOD OF USE

RELATED APPLICATION

This application is a divisional of U.S. application Ser. No. 16/391,843, filed on Apr. 23, 2019, which is a continuation of International Application No. PCT/US2018/019353, which designated the United States and was filed on Feb. 23, 2018, published in English, and claims the benefit of U.S. Provisional Application No. 62/463,049, filed on Feb. 24, 2017. The entire teachings of the above applications are incorporated herein by reference.

BACKGROUND

Fenestrated endovascular aortic repair (FEVAR) is a minimally invasive procedure to treat aortic aneurysms that span blood vessels arising from the aorta that supply blood to vital organs including the kidneys, intestine and liver. Endovascular grafts employed in FEVAR define fenestrations for insertion of branch prostheses that serve as passageways for blood flow through arterial branches to vital organs following implantation of the endovascular graft. Maximizing blood flow to vital organs and minimizing endoleaks following repair of aneurysms with fenestrated vascular prostheses, such as juxtarenal aortic aneurysms and short-neck abdominal aortic aneurysms, present medical challenges that must be overcome if additional surgical intervention is to be avoided.

Therefore, a need exits for new and improved endovascular repair devices and methods to treat arterial pathologies, such as juxtarenal and short-neck abdominal aortic aneurysms.

SUMMARY OF THE INVENTION

The present invention relates to a vascular prosthesis and a method for its use in treating and repairing arterial vascular damage, such as vascular damage associated with aortic aneurysms and regions of the aorta having arterial branches that supply blood to vital organs and tissues including juxtarenal remote aortic aneurysms and short-neck abdominal aortic aneurysms.

In one embodiment the invention is a vascular prosthesis that includes a luminal graft component, at least one support disk, and a moveable disk. The luminal graft component has a proximal open-end, a distal open end, and defines a main lumen extending from the proximal open end to the distal open end, the luminal graft component defining an outside surface, an inside surface, and at least one graft fenestration. At least one support disk defines a support disk fenestration, wherein the support disk is fixed to the luminal graft component at the graft fenestration, and the support disk fenestration substantially aligns with the graft fenestration. The moveable disk has a diameter greater than that of the support disk fenestration and defines an opening having a diameter smaller than that of the graft fenestration and the support disk fenestration. The moveable disk is moveable between the support disk and the luminal graft component, or between two of the support disks.

In another embodiment, the invention is a method for treating an aortic aneurysm and includes the step of delivering a vascular prosthesis through an artery to the aneurysm of a patient, the aneurysm spanning a region of the artery that includes at least one arterial branch, the vascular prosthesis being radially and releasably constrained by a vascular prosthesis delivery device. The vascular prosthesis includes a luminal graft component having a proximal open end, a distal open end, and defines a main lumen extending from the proximal open end to the distal open end. The luminal graft component defines an outside surface, an inside surface, at least one graft fenestration. The at least one support disk defines a support disk fenestration, wherein the support disk is fixed to the luminal graft component at the graft fenestration, and the support disk fenestration is substantially aligned with the graft fenestration. A moveable disk has a diameter greater than that of the support disk fenestration and defines an opening having a diameter smaller than that of the graft fenestration and the support disk fenestration. The moveable disk is moveable between the support disk and the luminal graft component, or between two of the support disks. At least one support disk fenestration is substantially aligned with at least one arterial branch at the aneurysm of the patient. The vascular prosthesis is at least partially released from the vascular prosthesis delivery device, and at least one branch prosthesis is delivered through the proximal open end or the distal open end of the luminal graft component of the vascular prosthesis, into the main lumen of the luminal graft component, and then through the graft fenestration, the support disk fenestration, and the moveable disk opening, and then a distal end or a proximal end of the branch prosthesis is delivered into at least one arterial branch, thereby treating the aneurysm.

The vascular prostheses of the invention have several advantages by, for example, providing the surgeon with increased flexibility to accommodate anatomical variations in the position of arterial branches at an aneurysm. Specifically, the portion of a fenestration of a luminal graft component of a vascular prosthesis can be adjusted to better fit a branch prosthesis during implantation by employing the vascular prosthesis and method of the invention. The vascular prosthesis of the invention has the additional advantage of improving stability between the fenestration of the vascular prosthesis of the invention and a branch prosthesis following insertion of the branch prosthesis into the fenestration, and of better securing the branch prosthesis within an appropriately sized fenestration for the branch prosthesis, without having to correct for uncertain alignment within an arterial branch, thereby significantly reducing the incidence and severity of endoleaks, branch vessel occlusion and resulting complications.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION OF THE INVENTION

The features and other details of the invention, either as steps of the invention or as combinations of parts of the invention will now be more particularly described and pointed out in the claims. It will be understood that the particular embodiments of the invention are shown by way of illustration and not as limitations of the invention. The principle features of this invention can be employed in various embodiments without departing from the scope of the invention. It is to be understood that the same numerals in different drawings and embodiments of this invention reference the same component part.

The invention is generally directed to stent grafts for use in treating and repairing aortic vascular damage, such as vascular damage associated with an aortic aneurysm in regions of the aorta having arterial branches to vital organs and tissues, such as thoracic aortic aneurysms, abdominal aortic aneurysms, thoraco-abdominal aortic aneurysms, including juxtarenal aortic aneurysms and short-neck abdominal aortic aneurysms.

A description of example embodiments of the invention follows.

When reference is made herein to a prosthesis, also referred to herein as "stent graft," "stent graft prosthesis," and "vascular prosthesis," to be delivered, or implanted in a patient, the word "proximal" means that portion of the prosthesis or component of the prosthesis that is relatively close to the heart of the patient and "distal" means that portion of the prosthesis or component of the prosthesis that is relatively far from the heart of the patient. A "longitudinal axis," as that term is defined herein, means an axis along a lengthwise direction of a body that also passes through a center of gravity of the body.

When, however, reference is made to a delivery system or a component of a delivery system employed to deliver, or implant, a prosthesis, the word, "proximal," as employed herein, means closer to the clinician using the delivery system. When reference is made to a delivery system or a component of a delivery system, "distal," as that term is employed herein, means, further away from the clinician using the delivery system.

For clarity, the word "proximate" means "close to," as opposed to the meanings ascribed to "proximal" or "distal" described above with respect to either the prosthesis or a delivery system.

Figure 1:
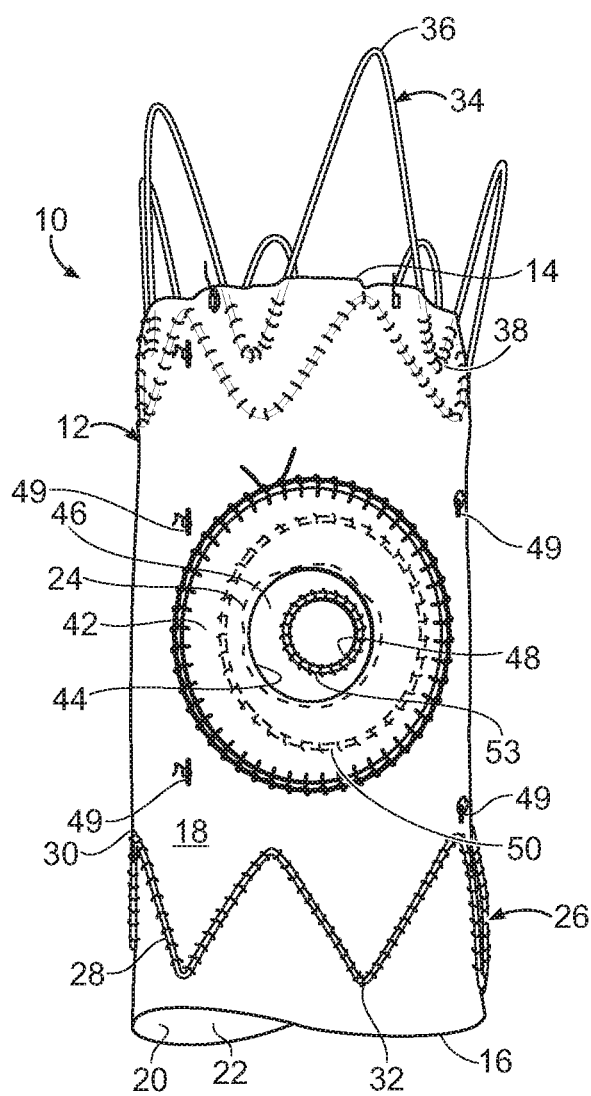
FIG. 1 is a side view of one embodiment of a vascular prosthesis of the invention.
Figure 2:
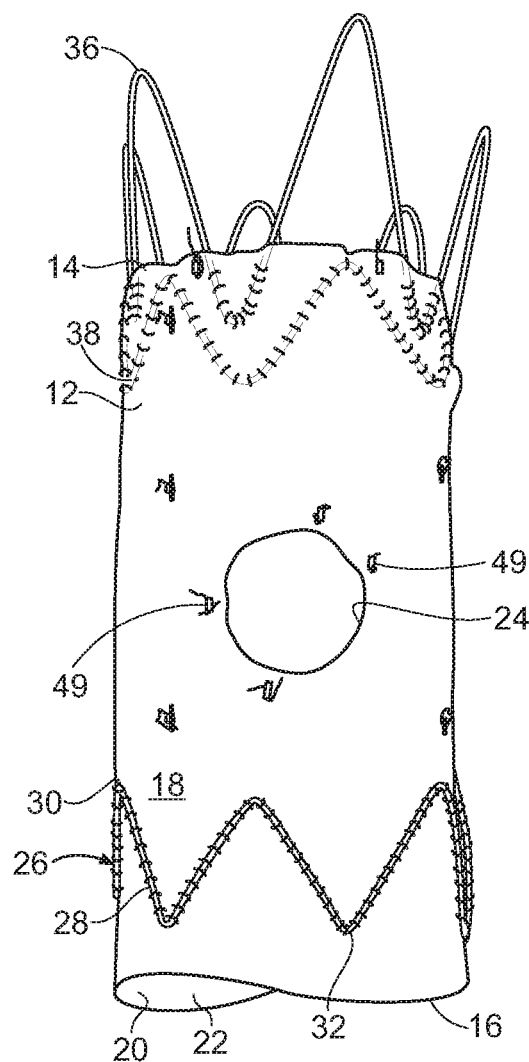
FIG. 2 is a side view of the vascular prosthesis of FIG. 1, without the presence of an external support disk or a moveable disk.

One embodiment of the vascular prosthesis of the invention is shown in FIGS. 1 and 2. As shown therein, vascular prosthesis 10 includes luminal graft component 12 having proximal open end 14, distal open end 16, outside surface 18, and inside surface 20. Inside surface 20 defines main lumen 22 extending from proximal open end 14 to distal open end 16. Luminal graft component 12 defines fenestration 24. Luminal graft component 12 is formed of a suitable material, such as is known to those skilled in the art, including, for example, at least one member of the group consisting of expanded polytetrafluoroethylene (PTFE), such as ePTFE, and polyethylene terephthalate (PET), such as woven polyester.

Stents 26 extend longitudinally along outside surface 18 of luminal graft component 12, and include struts 28 that join at opposite ends to define proximal apices 30 and distal apices 32. Optional bare stent 34 at proximal end 14 includes proximal apices 36 and distal apices 38, and is fixed to inside surface 20 of luminal graft component 12 at distal apices 38. Stents 26 and bare stent 34 are formed of a suitable material known to those skilled in the art, such as Nitinol or some other suitable shape memory alloy. Optionally, radiopaque markers 49, such as those known to those skilled in the art, are secured, such as by suturing or employing a biocompatible adhesive, to luminal graft component 12.

Support disk 42 defines support disk fenestration 44 that encompasses fenestration 24 and is fixed to luminal graft component 12. Support disk 42 is formed of a suitable material, such as Nitinol or some other suitable shape memory alloy, PTFE, PET, or silicone. Support disk 42 is fixed to outside surface 18 of luminal graft component 12 by, for example, sutures or by use of a suitable biocompatible adhesive, such as is known in the art. Moveable disk 46 defines opening 48 and lies between luminal graft component 12 and support disk 42.

Figure 3:
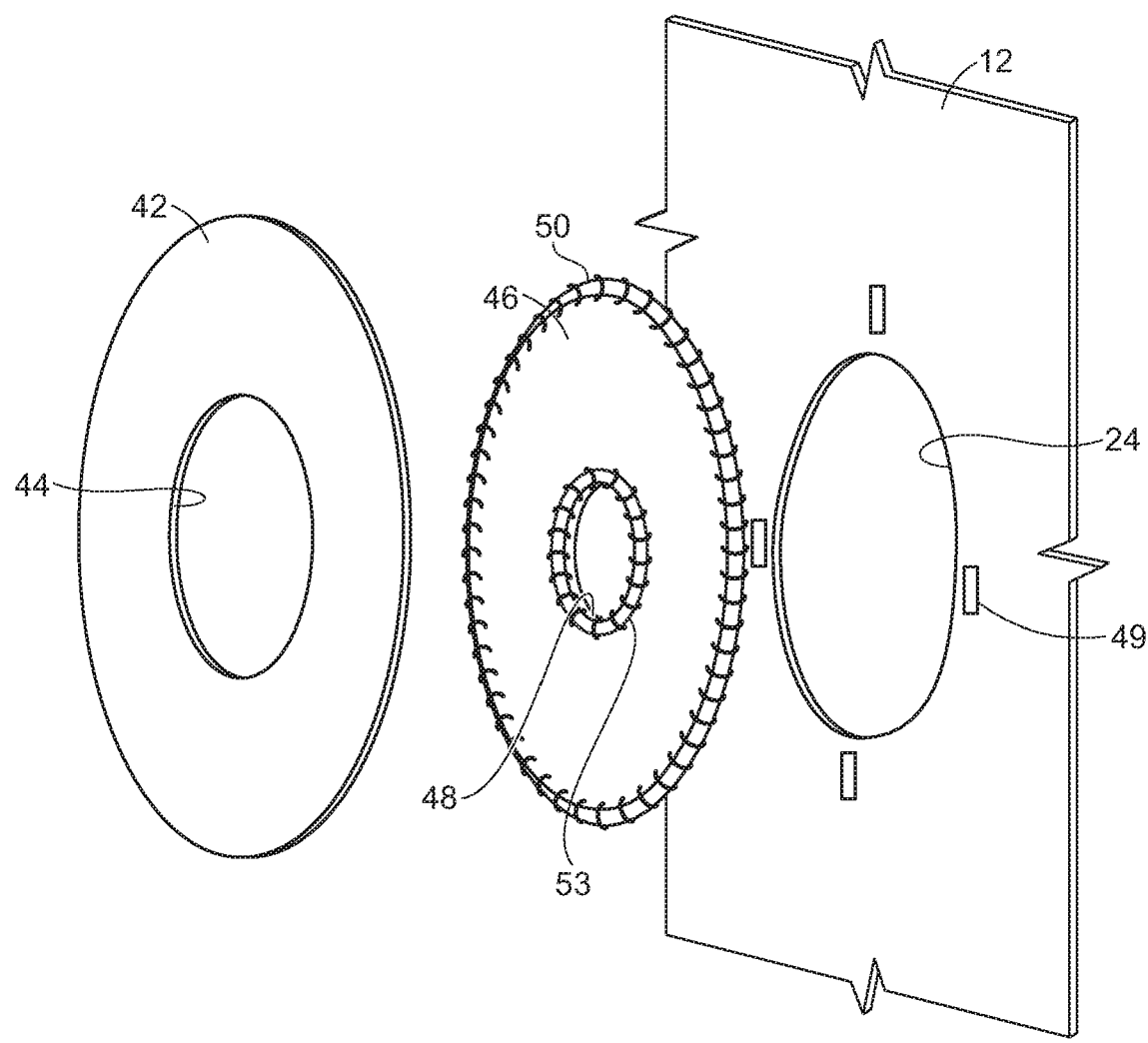
FIG. 3 is an exploded view of a detail of the vascular prosthesis of FIGS. 1 and 2, showing the relative placement of the support disk, the moveable disk, and a fenestration of a luminal graft component of the vascular prosthesis.

Optionally, ring 50 is secured to perimeter of moveable disk 46. Ring 50 is secured to perimeter of moveable disk by suitable means, such as is known in the art. As shown in FIG. 3, ring 50 is secured to perimeter of movable disk 46 by sutures. Attachment of ring 50 to perimeter of moveable disk 46 has the benefit of increasing resistance to movement of moveable disk 46, thereby preventing possible extraction of moveable disk 46 from between support disk 44 and luminal graft component 12 during implantation of a branch prosthesis (not shown). Examples of suitable materials of ring 50 secured to perimeter of moveable disk 46 include Nitinol or some other shape memory alloy, stainless steel, chromium cobalt and a polymer.

Although not shown, in an alternative embodiment, support disk 42 is fixed to inside surface 20 of luminal graft component 12, and moveable disk 46 is located between support disk 42 and luminal graft component 12. In either embodiment, fenestration 24, support disk fenestration 44, and moveable disk opening 48 are all aligned, and moveable disk 46 is moveable between luminal graft component 12 and support disk 42. Radiopaque markers 49 are fixed to luminal graft component 12 and distributed about fenestration 24. In an embodiment, at least one of support disk 42, moveable disc 46 and radiopaque markers 49 includes radiopaque material, such as at least one radiopacifier selected from the group consisting of barium sulfate, bismuth, tungsten, platinum, platinum-iridium, tantalum and tantalum-tungsten.

FIG. 2 is a side view of the vascular prosthesis 10 of FIG. 1 without support disk 42 or moveable disk 46, showing fenestration 24 and radiopaque markers 49. Luminal graft component 12 defines fenestration 24.

Figure 4:
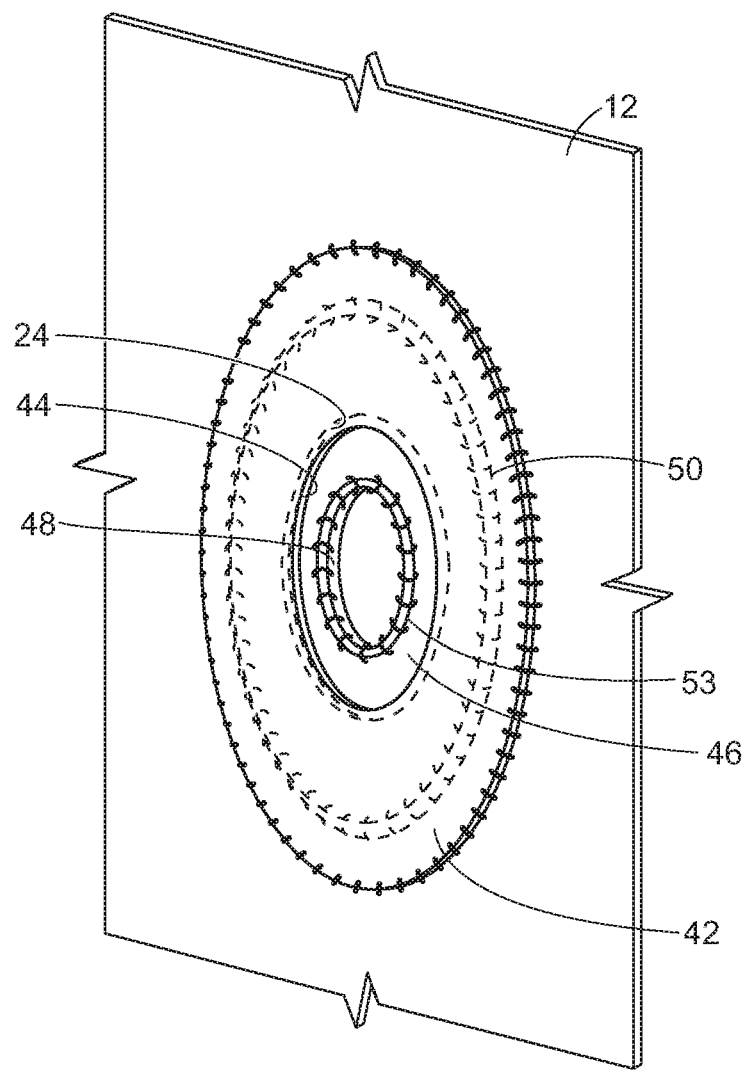
FIG. 4 is an assembled view in perspective of the detail of the vascular prosthesis of the invention shown in FIG. 3.

FIG. 3 is an expanded view in perspective of a detail of vascular prosthesis 10 of FIG. 1. As shown in FIG. 3, moveable disk 46 is located between luminal graft component 12 and support disk 42. Fenestration 24, support disk fenestration 44 and moveable disk opening 48 are aligned. FIG. 4 is a perspective view of the detail of FIG. 3, but in assembled form, showing moveable disk 46 sandwiched between support disk 42 and luminal graft component 12, and alignment of fenestration 24, support disk fenestration 44, and opening 48 of moveable disk 46. Opening 48 of moveable desk 46 can include ring 53, as also shown in FIG. 3.

Figure 5:
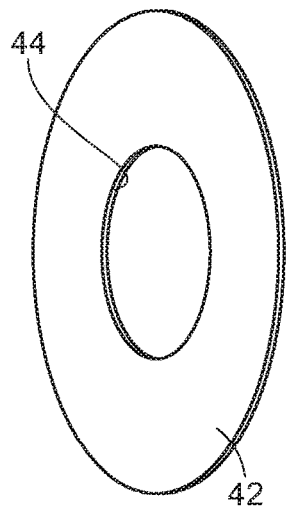
FIG. 5 is an exploded view in perspective of a detail of an alternative embodiment of the vascular prosthesis of the invention shown in FIGS. 1 and 2.
Figure 5:
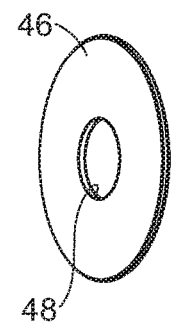
Figure 5:
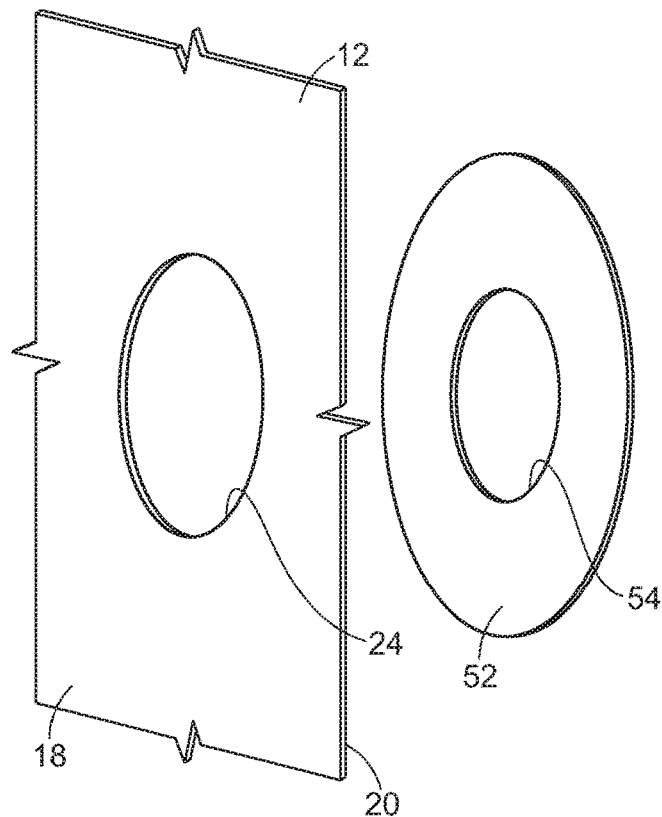
Figure 7:
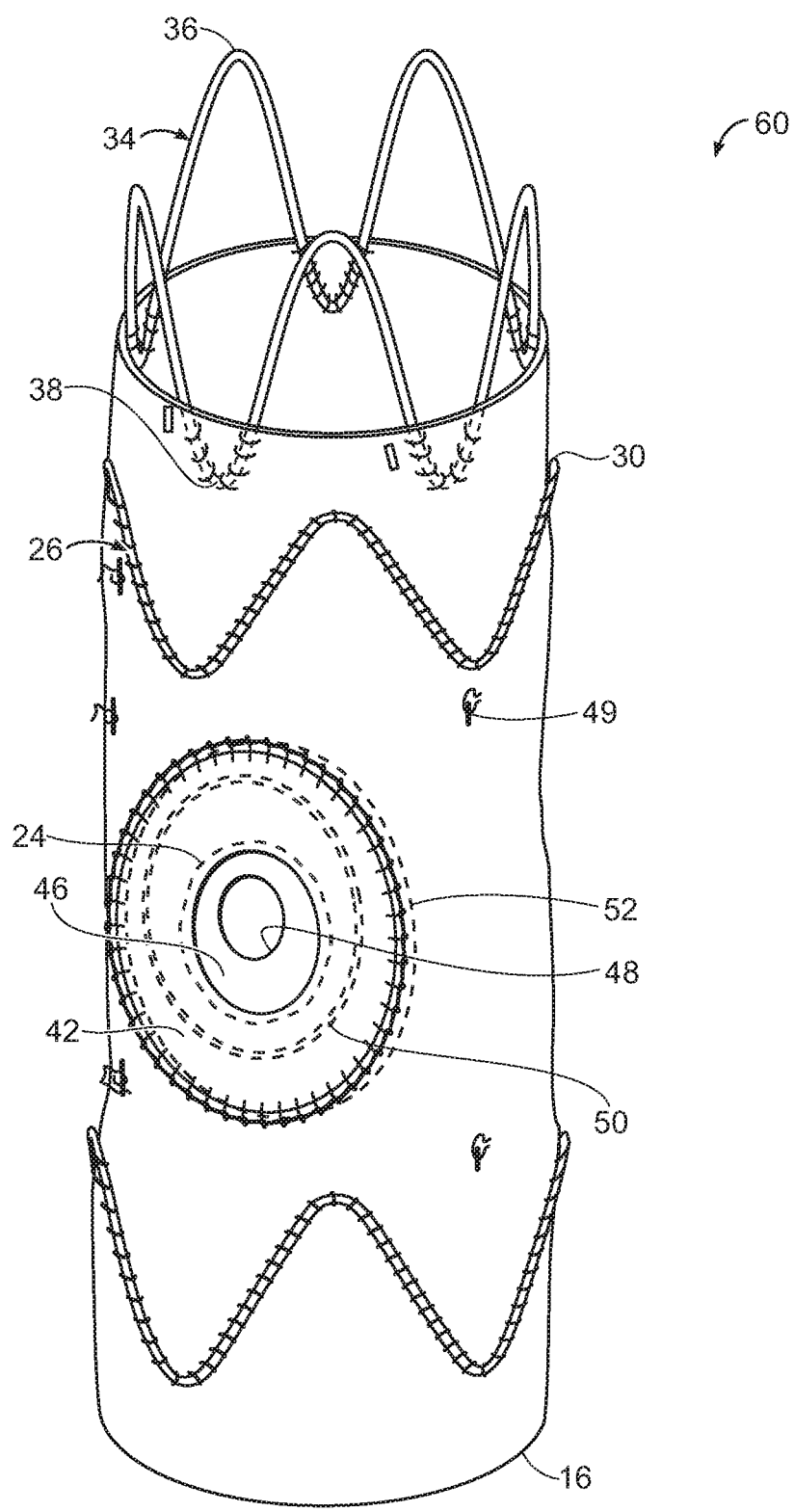
FIG. 7 is a perspective view of the vascular prosthesis of the invention represented in FIGS. 5, 6A, and 6B.

FIG. 5 is an exploded view of a detail of another embodiment of the vascular prosthesis of the invention, namely vascular prosthesis 60 shown in FIG. 7. As shown in FIG. 5, moveable disk 46 is located between two support disks 42,52, which define respective support disk fenestrations 44,54, and each of which is secured to luminal graft component 12, when assembled. While moveable disk 46 is shown between outside support disk 42 and inside support disk 52. It is to be understood that, alternatively, moveable disk 46 can be outside or inside luminal graft and still between support disks 42,52. As in the previous embodiment, and although not shown in the embodiment of FIG. 5, moveable disk 46 can include wire or ring 50 secured to the perimeter of moveable disk 46. In certain embodiments of the invention, the thickness of each of the disks of the at least one support disk 52 is in a range of between about 0.05 mm and about 0.50 mm, and the thickness of the moveable disk 46 is in a range of between about 0.05 mm and about 0.50 mm.

Figure 6A:
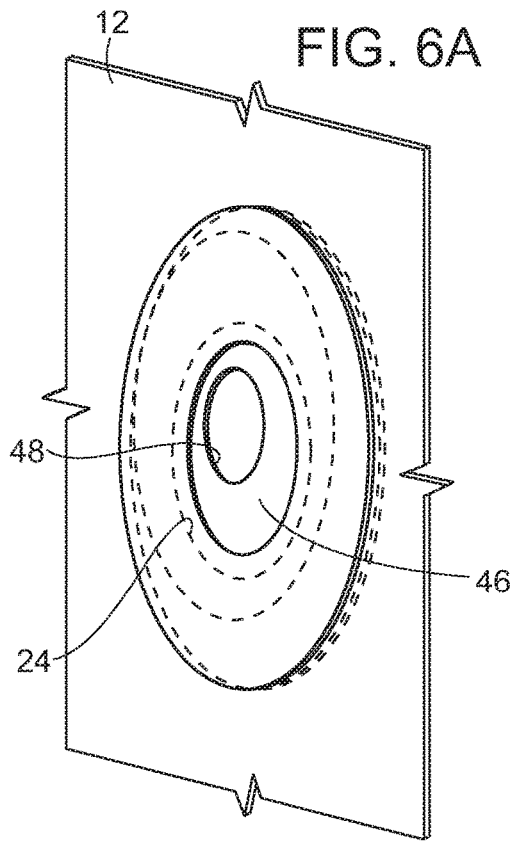
FIGS. 6A and 6B are assembled views in perspective of the component parts showing the details of the embodiment of the vascular prosthesis of FIG. 5, wherein the opening of the moveable disk moves within a support disk opening.
Figure 6B:
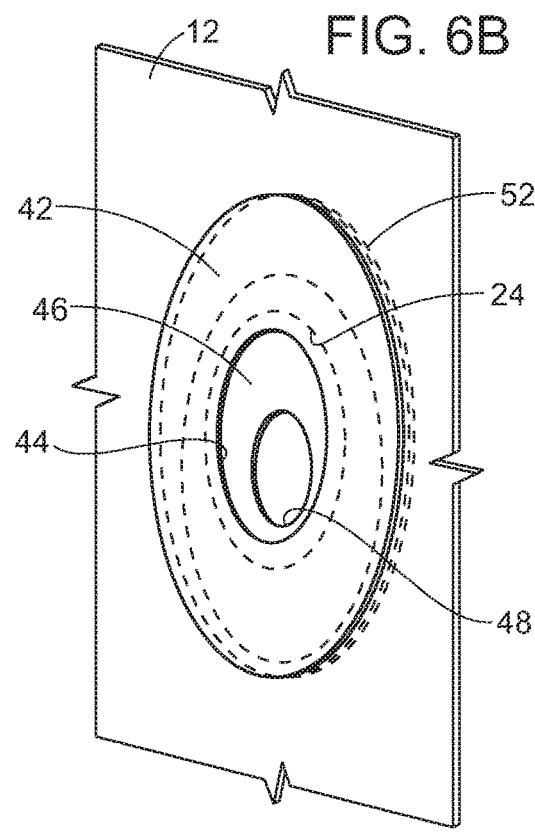

FIGS. 6A and 6B are perspective views of the detail shown in FIG. 5 of vascular prosthesis 60, in assembled form, showing that luminal graft component fenestration 24, support disk fenestrations 44,54 and moveable disk opening 48 are all aligned, while simultaneously allowing moveable disk 46 and, consequently, opening 48 to move between inside support disk 42 and outside support disk 52, thereby permitting improved alignment during implantation of a branch prosthesis (not shown) extending from within a luminal graft component lumen to an arterial branch.

FIG. 7 is a perspective view of vascular prosthesis 60, the detail of which is represented in FIGS. 5, 6A, and 6B, showing the embodiment of outside support disk 42, inside support disk 52 and moveable disk 46 sandwiched between them relative to the remainder of vascular prosthesis 60.

A method for treating an aorta aneurysm, according to embodiments of the invention, includes delivering a vascular prosthesis of the invention through an artery to an aneurysm of a patient, the aneurysm spanning a region of the artery that includes at least one arterial branch, the vascular prosthesis being radially and releasably constrained by vascular prosthesis delivery device. In another embodiment, the invention is a method of delivering and implanting a vascular prosthesis of the invention and a branch prosthesis at an aneurysm of a patient.

Figure 8:
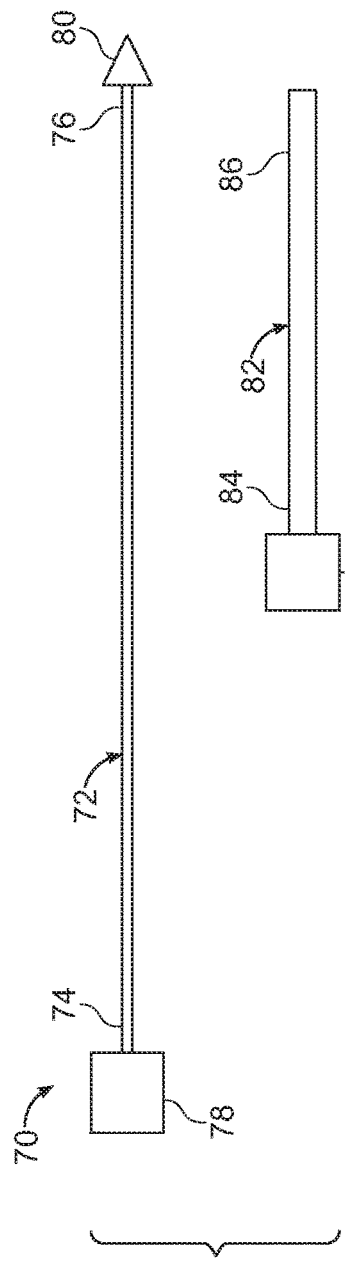
FIG. 8 is an exploded view of one embodiment of a prior art delivery device for delivering a vascular prosthesis of the invention.

FIG. 8 is an exploded side view of prior art delivery device suitable for delivering a vascular prosthesis of the invention. As can be seen in FIG. 8, delivery device 70 includes guidewire catheter 72 having proximal end 74 and distal end 76. Proximal handle 78 is fixed to proximal end 74 and nose cone 80 is fixed to distal end 76. Introducer sheath 82 has proximal end 84 and distal end 86. Distal handle 90 is fixed to proximal end 84. Introducer sheath 82 can be rigid or flexible.

Figure 9A:
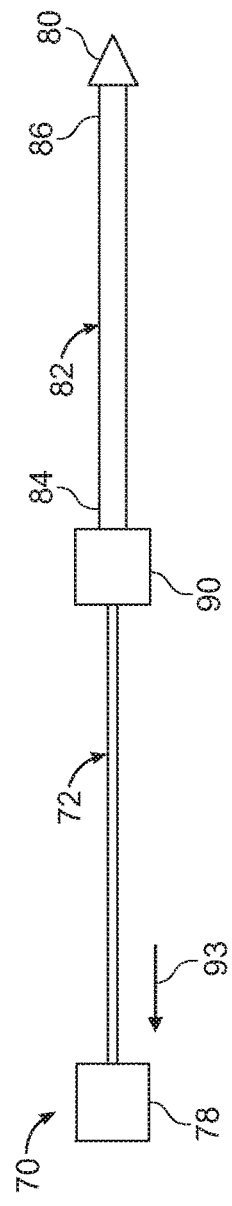
FIG. 9A is a side view of the delivery device shown in FIG. 8 and containing a vascular prosthesis of the invention (not shown) loaded within the introducer sheath of the delivery device.
Figure 9B:
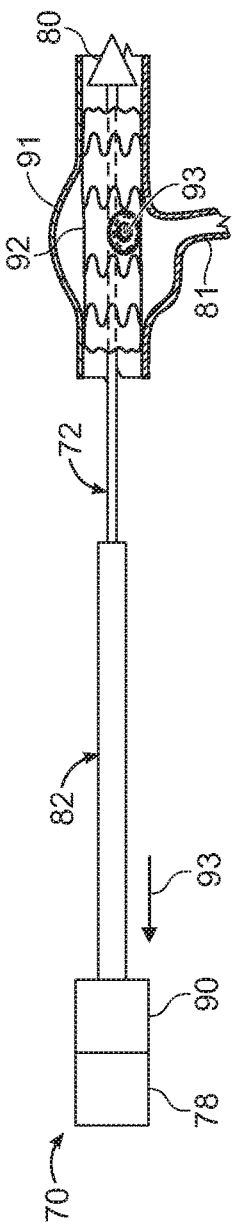
FIG. 9B is a side view of the delivery device shown in FIG. 9A, after retraction of an introducer sheath of the delivery device to expose a vascular prosthesis of the invention or a branch prosthesis during delivery to an aneurysm site.
Figure 9C:
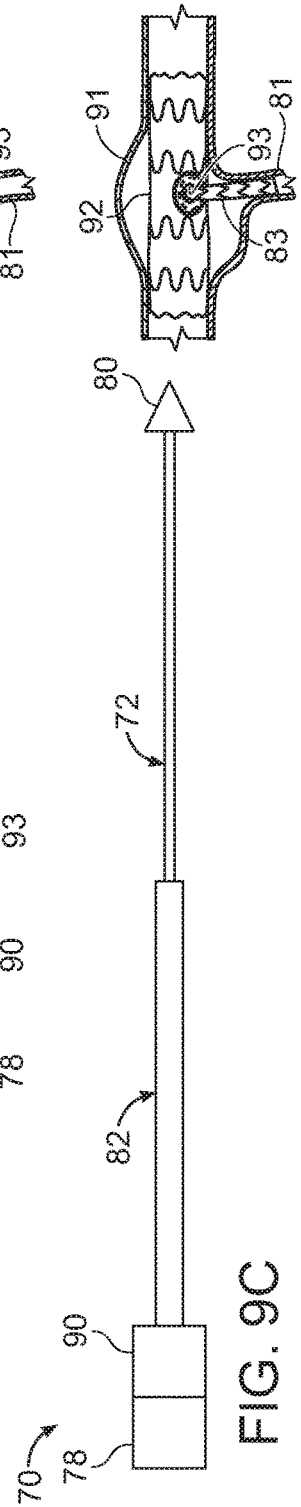
FIG. 9C is a side view of the delivery device and vascular prosthesis of FIG. 9B after retraction of the delivery device from the vascular prosthesis of the invention or the branch prosthesis, thereby completing implantation of the prosthesis.

FIG. 9A is a side view of the delivery device 70 when assembled. As can be seen therein, introducer sheath 82 and distal handle 90 extend around guidewire catheter 72. Although not shown, vascular prosthesis 92 of the invention is held in a radially constricted position around guidewire catheter 72 and within introducer sheath 82. Vascular prosthesis 92 is implanted at aneurysm 91 by advancing delivery device 70 within an artery of a patient until introducer sheath 82 is at the aneurysm 91. Distal handle 90 is then retracted along guidewire catheter 72 and toward proximal handle 74, indicated by arrow 93 as shown in FIG. 9B thereby retracting introducer sheath 82 from around vascular prosthesis 92. Vascular prosthesis 92, with support disk 93, is released from its radially constricted position and radially expands to a released position, such as by use of a balloon catheter, or by use self-expanding radial stents, as is known in the art. Vascular prosthesis 92 is thereby deployed at aneurysm 91. Delivery device 70 thereafter is removed from the patient, as shown in FIG. 9C, thereby completing implantation of vascular prosthesis 70 and treatment of aneurysm 91. The same or a similar delivery device can be employed to deliver or implant one or more branch prostheses through respective fenestrations of a vascular prosthesis of the invention. For example, implantation of branch prosthesis 83 through fenestration 93 and into branch artery 81. It is to be understood that, alternatively, other suitable types of aortic prosthesis delivery devices, such as are known in the art, can be employed.

Figure 10:
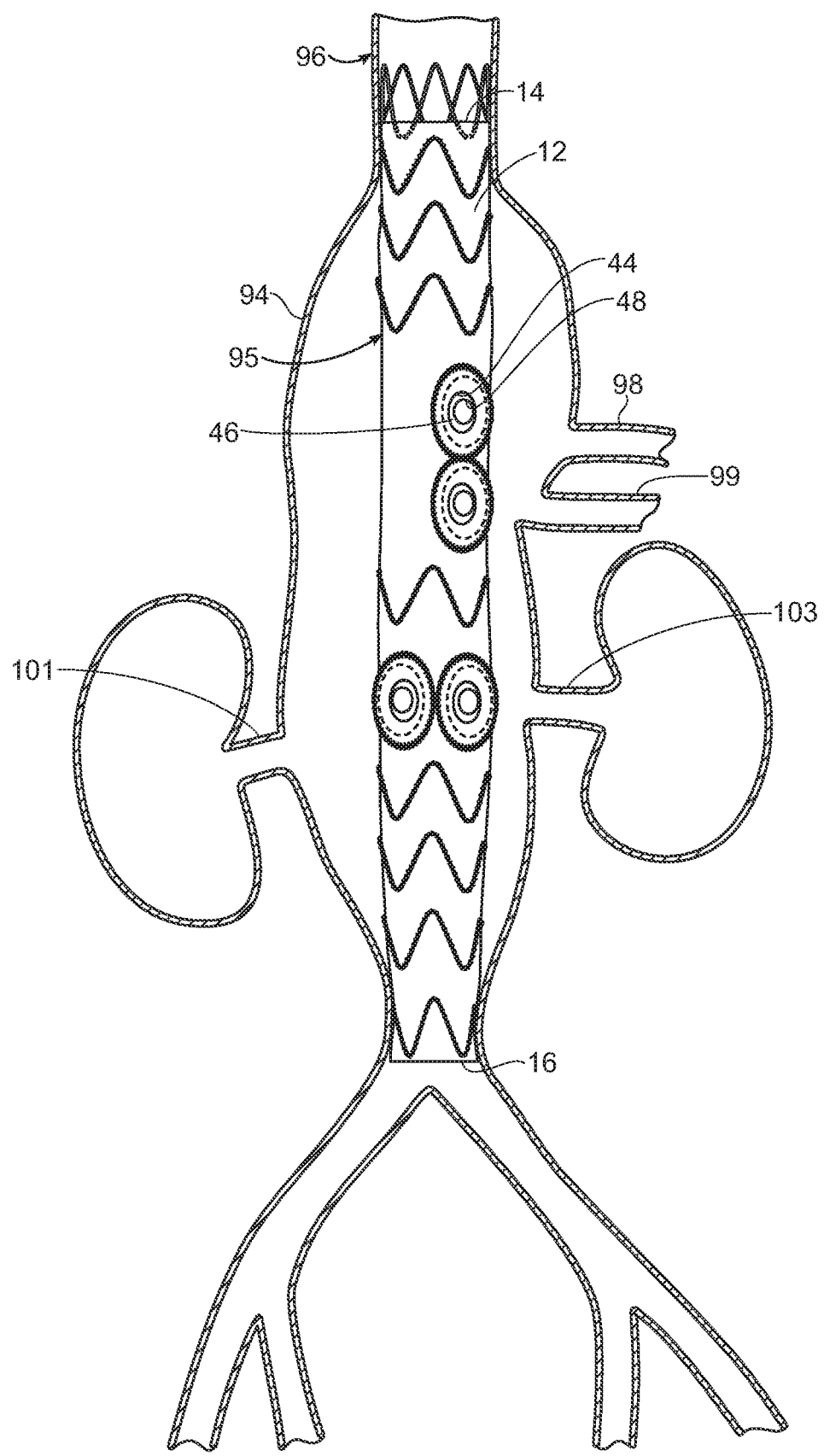
FIG. 10 is a side view of an embodiment of a vascular prosthesis of the invention implanted in an aorta of a subject.

FIG. 10 is a side view of vascular prosthesis 95 of the invention at aneurysm 94 at artery 96 of a patient, showing incomplete alignment of moveable disk opening 48 with arterial branch 98.

Figure 11:
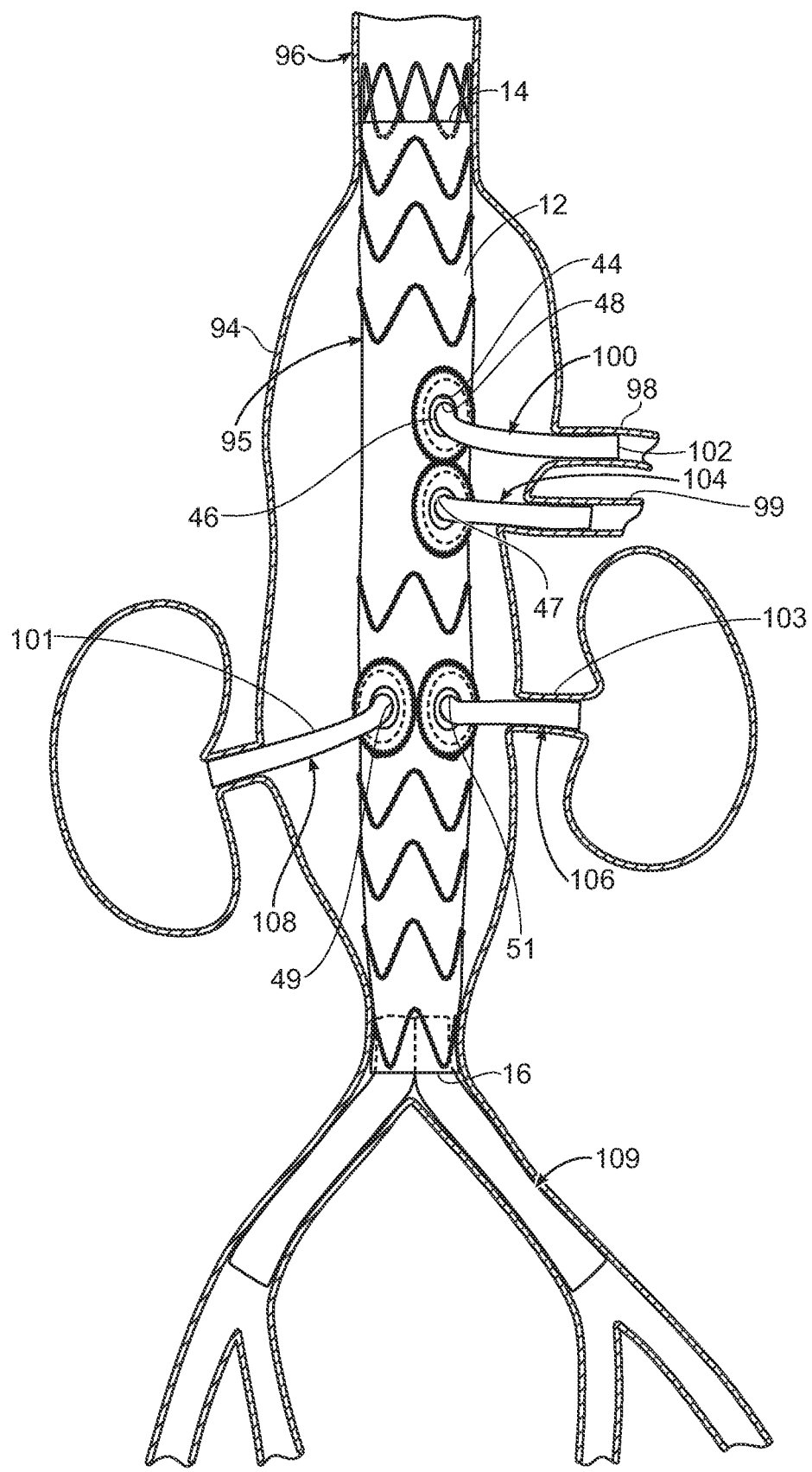
FIG. 11 is a side view of a vascular prosthesis of the invention, wherein branch prostheses have been implanted through respective fenestrations, support and moveable discs of the vascular prostheses of the invention.

With reference to FIG. 11, at least one support disk fenestration 44 of the vascular prosthesis 95 is substantially aligned with at least one arterial branch 98 (celiac artery) at aneurysm 94 of the patient. Vascular prosthesis 95 is at least partially released from the vascular prosthesis delivery device. Branch prosthesis 100 is then delivered through proximal open end 14 or distal open end 16 of the luminal graft component 12 of vascular prosthesis 95, and through graft fenestration 24, support disk fenestration 54, and moveable disk opening 48 into main lumen 22 of the luminal graft component 12. Distal end 102 of branch prosthesis 100 is then delivered into at least one arterial branch 98, thereby treating aneurysm 94. During implantation of branch prosthesis 100 through moveable disk opening 48 and into arterial branch 98, moveable disk 46 shifts within support disk fenestration 54 as illustrated, for example, in FIGS. 6A and 6B, to thereby improve alignment of distal end 102 of branch prosthesis 100 with arterial branch 98 without intervention by the surgeon.

As can be seen in FIG. 11, branch prostheses 100,104, 106,108 are delivered through each of moveable disk opening 47,48,49,51 and into arterial branches 98,99,101,103 of aorta 96 at the aneurysm site 94, whereby moveable disks 47,48,49,51 have shifted as a consequence of implantation of branch prosthesis 100,104,106,108 to better align the respective moveable disk openings with the celiac artery 98, superior mesenteric artery 99, right renal artery 101 and left renal artery 103. Alignment of the respective moveable disk openings occurs as a consequence of implantation and does not require independent adjustment, apart from implantation of branch prostheses 100,104,106,108, by the surgeon. Additional branch prostheses 109 can be implanted into the distal end of vascular repair device 60.

Although not shown, the vascular repair device of the invention can be bifurcated and additional branch prostheses can be added to the bifurcated distal end of the vascular prostheses of the invention.

Vascular prostheses of the invention can be implanted, for example, by transfemoral access. Additional branch prostheses that are directed into the vascular prostheses of the invention can be implanted, for example, by supraaortic vessel access (e.g., through the brachial artery or axillary access), or by transfemoral access, or access from some other branch or branch of major blood vessels, including peripheral blood vessels.

The teachings of all patents, published applications and references cited herein are incorporated by reference in their entirety. The relevant teachings of U.S. Pat. Nos. 8,292,943; 7,763,063; 8,308,790; 8,070,790; 8,740,963; 8,007,605; 9,320,631; 8,062,349; 9,198,786; 8,062,345; 9,561,124; 9,173,755; 8,449,595; 8,636,788; 9,333,104; 9,408,734; 9,408,735; 8,500,792; 9,220,617; 9,364,314; 9,101,506; 8,998,970; 9,554,929; 9,439,751; 9,592,112; 9,655,712; 9,827,123, 9,877,857, 9,907,686; U.S. patent application Ser. No. 14/575,673; Ser. No. 15/166,818; Ser. No. 15/167,055; Ser. No. 14/272,818; Ser. No. 14/861,479; Ser. No. 15/478,424; Ser. No. 15/478,737; Ser. No. 15/587,664; Ser. No. 15/604,032; Ser. No. 15/672,404; Ser. No. 15/816,772; Ser. No. 15/839,272; Ser. No. 15/417,467; PCT/US2017/025844; PCT/US2017/025849; PCT/US2017/025912; PCT/US2017/034223 and PCT/US2017/046062, are also incorporated by reference in their entirety.

The relevant teachings of the PCT/US2018/019355; PCT/US2018/019344; PCT/US2018/019349; PCT/US2018/019354; PCT/US2018/019352; PCT/US2018/019342; PCT/US2018/019350; PCT/US2018/019356; PCT/US2018/019351; and PCT/US2018/019510, are also incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A method for treating arterial vascular damage, comprising the steps of:
    a) delivering a vascular prosthesis through an artery to an aneurysm site of a patient, the aneurysm site spanning a region of the artery that includes at least one arterial branch, the vascular prosthesis being radially and releasably constrained by a vascular prosthesis delivery device, the vascular prosthesis including:
        i. a luminal graft component having a proximal open end, a distal open end, and defining a main lumen extending from the proximal open end to the distal open end, the luminal graft component defining an outside surface, an inside surface, and at least one graft fenestration,
        ii. at least one support disk defining a support disk fenestration, wherein the at least one support disk is fixed to the luminal graft component at the at least one graft fenestration, and the at least one support disk fenestration substantially aligns with the at least one graft fenestration,
        iii. a moveable disk, the moveable disk having a diameter greater than a diameter of the at least one support disk fenestration and defining an opening having a diameter smaller than that of the at least one graft fenestration and the at least one support disk fenestration, the moveable disk being moveable between the at least one support disk and the luminal graft component, or between two of the support disks,
        iv. a perimeter ring affixed to the perimeter of the moveable disk, the perimeter ring increasing the resistance to movement of the moveable disk, thereby preventing extracting of the moveable disk from between at least one the support disk and the luminal graft component, or between two of the support disks; and
    b) substantially aligning the at least one support disk fenestration with the at least one arterial branch at the aneurysm site of the patient;
    c) at least partially releasing the vascular prosthesis from the vascular prosthesis delivery device;
    d) delivering at least one branch prosthesis through the proximal open end or the distal open end of the luminal graft component of the vascular prosthesis and the at least one graft fenestration, the at least one support disk fenestration, and the moveable disk fenestration to the at least one arterial branch, the at least one branch prosthesis being radially and releasably constrained by a branch prosthesis delivery system; and
    e) releasing the at least one branch prosthesis from the branch prosthesis delivery device, whereby expansion of the at least one branch prosthesis causes the moveable disk to shift within a support disk fenestration, thereby aligning the proximal open end or a distal open end of the at least one branch prosthesis with the at least one arterial branch, thereby treating the aortic aneurysm.

2. The method of claim 1, wherein the moveable disk is between the luminal graft component and the at least one support disk.

3. The method of claim 2, wherein the at least one support disk is fixed to the outside surface of the luminal graft component.

4. The method of claim 2, wherein the at least one support disk is fixed to the inside surface of the luminal graft component.

5. The method of claim 1, wherein the at least one support disk is at least one pair of support disks.

6. The method of claim 5, wherein the at least one pair of support disks are on opposite sides of the luminal graft component, and the moveable disk is between the at least one pair of support disks.

7. The method of claim 6, wherein the at least one pair of support disks is sewn to the luminal graft component.

8. The method of claim 1, wherein the at least one support disk includes at least one material of the group consisting of polyethylene terephthalate (PET), expanded polytetetrafluroethylene (ePTFE), silicone, polyurethane, and a shape-memory alloy.

9. The method of claim 1, wherein the moveable disk includes at least one material of the group consisting of polyethylene terephthalate (PET), expanded polytetetrafluroethylene (ePTFE), silicone, polyurethane, and a shape-memory alloy.

10. The method of claim 1, wherein a thickness of the at least one support disk is in a range of between about 0.05 mm and about 0.50 mm and the thickness of the moveable disk is in a range of between about 0.05 mm and about 0.50 mm.

11. The method of claim 1, further including an opening ring affixed to the moveable disk at the opening of the moveable disk.

12. The method of claim 11, wherein the opening ring includes a shape-memory alloy.

13. The method of claim 12, wherein the shape-memory alloy is Nitinol.

14. The method of claim 1, wherein the perimeter ring includes a shape memory alloy.

15. The method of claim 14, wherein the shape memory alloy is Nitinol.

16. The method of claim 1, further including a second branch prosthesis, the second branch prosthesis extending through an opening of a second moveable disk, a second support disk fenestration and a second graft fenestration and into the main lumen of the luminal graft component.

* * * * *